(12) United States Patent
Guo et al.

(10) Patent No.: US 12,404,486 B1
(45) Date of Patent: Sep. 2, 2025

(54) *ASPERGILLUS ORYZAE* JAAS-32 AND USE THEREOF IN PREPARATION OF LARVAL *HERMETIA ILLUCENS* PASTE PROTEIN PEPTIDE

(71) Applicant: Jiangsu Academy of Agricultural Sciences, Nanjing (CN)

(72) Inventors: Ting Guo, Nanjing (CN); Xiaomei Ye, Nanjing (CN); Jing Du, Nanjing (CN); Cong Wang, Nanjing (CN); Yonglan Xi, Nanjing (CN); Xiangping Kong, Nanjing (CN); Fei Zhu, Nanjing (CN)

(73) Assignee: Jiangsu Academy of Agricultural Sciences, Nanjing (CN)

( * ) Notice: Subject to any disclaimer, the term of this patent is extended or adjusted under 35 U.S.C. 154(b) by 0 days.

(21) Appl. No.: 18/946,341

(22) Filed: Nov. 13, 2024

(30) Foreign Application Priority Data

Mar. 4, 2024 (CN) .......................... 202410238451.2

(51) Int. Cl.
| | | |
|---|---|---|
| *C12N 1/14* | (2006.01) | |
| *A01N 37/46* | (2006.01) | |
| *C07K 14/435* | (2006.01) | |
| *C12N 9/62* | (2006.01) | |
| *C12P 21/00* | (2006.01) | |
| *C12R 1/69* | (2006.01) | |

(52) U.S. Cl.
CPC ............. *C12N 1/145* (2021.05); *A01N 37/46* (2013.01); *C07K 14/43577* (2013.01); *C12N 9/62* (2013.01); *C12P 21/00* (2013.01); *C12R 2001/69* (2021.05)

(58) Field of Classification Search
CPC ...................................................... C12N 1/00
See application file for complete search history.

(56) References Cited

U.S. PATENT DOCUMENTS

2022/0312797 A1  10/2022  Pipan

FOREIGN PATENT DOCUMENTS

| CN | 107986830 A | 5/2018 |
| CN | 111876456 A | 11/2020 |
| CN | 112544783 A | 3/2021 |

OTHER PUBLICATIONS

Li, Dongbao; "Hu Wenfeng: Using microorganisms and black soldier flies to treat livestock and poultry manure can continuously improve its utilization profits," Northern Animal Husbandry; Oct. 20, 2016; 2 pages; vol. 20.

*Primary Examiner* — Robert J Yamasaki
(74) *Attorney, Agent, or Firm* — Muncy, Geissler, Olds & Lowe, P.C.

(57) ABSTRACT

The present invention discloses an *Aspergillus oryzae* JAAS-32 and use thereof in preparation of a larval Hermetia illucens paste protein peptide. The *Aspergillus oryzae* JAAS-32 was deposited in Guangdong Microbial Culture Collection Center (GDMCC) on Aug. 10, 2023 with an accession number of GDMCC No: 63725, classified and named *Aspergillus oryzae*. A larval Hermetia illucens paste is subjected to enzymatic fermentation by the *Aspergillus oryzae* JAAS-32 provided by the present invention for 20-40 hours. The content of the protein peptide (<10 kDa) is 1.53 times that of an untreated group; the content of free amino acids is 1.41 times that of the untreated group; the total antioxidant activity is 1.35 times that of the untreated group. Diameters of inhibition zones against *Staphylococcus aureus*, *Escherichia coli*, and *Vibrio alginolyticus* are 1.62, 1.17, and 1.45 times those of the untreated group, respectively. The strain is cultured readily, fast in growth, and well-adapted. A low-cost, easy-to-operate, and efficient method for enhancing antibacterial performance of the larval Hermetia illucens paste can be established on the basis of the strain.

4 Claims, 3 Drawing Sheets

Specification includes a Sequence Listing.

SEQUENCE LISTING

```
Sequence total quantity: 3
SEQ ID NO: 1            moltype = DNA  length = 19
FEATURE                 Location/Qualifiers
source                  1..19
                        mol_type = other DNA
                        organism = synthetic construct
SEQUENCE: 1
tccgtaggtg aacctgcgg                                                  19

SEQ ID NO: 2            moltype = DNA  length = 20
FEATURE                 Location/Qualifiers
source                  1..20
                        mol_type = other DNA
                        organism = synthetic construct
SEQUENCE: 2
tcctccgctt attgatatgc                                                 20

SEQ ID NO: 3            moltype = DNA  length = 1003
FEATURE                 Location/Qualifiers
source                  1..1003
                        mol_type = genomic DNA
                        organism = Aspergillus oryzae
SEQUENCE: 3
gatttctcgt aaggtgccga gcgggtcatc atagaaacac cgcccgatcc ctagtcggca      60
tagtttatgg ttaagactac gacggtatct gatcgtcttc gatccctaa ctttcgttcc     120
ctgattaatg aaaacatcct tggcgaatgc tttcgcagta gttagtcttc agcaaatcca    180
agaatttcac ctctgacagc tgaatactga cgcccccgac tatccctatt aatcattacg    240
gcggtcctag aaaccaacaa aatagaaccg cacgtcctat tctattattc catgctaatg    300
tattcgagca aaggcctgct ttgaacactc taattttttc acagtaaaag tcctggttcc    360
ccccacagcc agtgaaggcc atgaggttcc cagaaggaa aggtccagcc ggaccagtac     420
tcgcggtgag gcggaccggc cagccagacc caaggttcaa ctacgagctt tttaactgca    480
acaactttaa tatacgctat tggagctgga attaccgcgg ctgctggcac cagacttgcc    540
ctccaattgt tcctcgttaa gggatttaga ttgtactcat tccaattacg agacccaaaa    600
gagcccccgta tcagtattta ttgtcactac ctccccgtgt cgggattggg taatttgcgc    660
gcctgctgcc ttccttggat gtgggtagcc cgtttctcag gctccctctc cggaatcgaa    720
ccctaattcc ccgttacccg ttgccaccat ggtaggccac tatcctacca tcgaaagttg    780
atagggcaga aatttgaatg aaccatcgcc ggcgcaaggc catgcgattc gttaagttat    840
tatgaatcac caaggagccc cgaagggcat tggttttta tctaataaat acaccccttc     900
cgaagtcgag gttttagca tgtattagct ctagaattac cacaggtatc catgtagtaa     960
ggtactatca aataaacgat aactgattta atgagccatt cgc                     1003
```

ASPERGILLUS ORYZAE JAAS-32 AND USE THEREOF IN PREPARATION OF LARVAL HERMETIA ILLUCENS PASTE PROTEIN PEPTIDE

REFERENCE TO AN ELECTRONIC SEQUENCE LISTING

The contents of the electronic sequence listing (Sequence Listing.xml; Size: 4,582 bytes; and Date of Creation: Feb. 6, 2025) is herein incorporated by reference in its entirety.

FIELD OF TECHNOLOGY

The present invention belongs to the technical field of biological formulations, and specifically relates to an *Aspergillus oryzae* JAAS-32 and use thereof in preparation of a larval Hermetia illucens paste protein peptide.

BACKGROUND

Abuse of antibiotics leads to the enhanced drug resistance of pathogenic bacteria and expedites the birth of "super drug-resistance bacteria". Antibiotic resistance and safety have been classified by the World Health Organization as one of the threats to the global public health. Therefore, there is an urgent need for seeking green, safe, and efficient antibiotic substitutes in the industry.

Antibacterial peptides are usually small-molecular polypeptides consisting of multiple amino acid residues, and have quite strong thermal stability, water solubility, broad-spectrum and efficient antibacterial activity. The antibacterial mechanism of antibacterial peptides is different from antibiotics, and it is thus not prone to produce drug-resistant strains. The insect-derived antibacterial peptide has good antibacteral activity, stability and safety, and thus is considered as one of the potential antibiotic substitutes and has already become a hot spot.

Hermetia illucens is a kind of insect, Hermetia, Stratiomyidae, Diptera. Its larvae can transform organic solid wastes such as kitchen wastes, livestock excrements, and waste crops to be rich in proteins and fat. Hermetia illucens larva is a kind of high-quality protein source, rich in various amino acids required by animals, and also it is a kind of good feed additive for various cultured animals and pets; for example, it has been reported in lots of patents, e.g., a Chinese patent CN112544783A. Hermetia illucens is rich in natural substances having bioactive components, including antibacterial peptides, antioxidants, immunomodulatory factors, and the like.

Therefore, how to improve the content and antibacterial performance of the antibacterial peptide in the larval Hermetia illucens paste is the core competitiveness for Hermetia illucens larvae to be antibiotic substitutes.

SUMMARY

Directed to the shortcomings of prior art, the technical problem to be solved in the present invention is to provide an *Aspergillus oryzae* JAAS-32 and use thereof in preparation of a larval Hermetia illucens paste protein peptide. The content and antibacterial performance of the protein peptide in the larval Hermetia illucens paste can be improved by treating the larval Hermetia illucens paste with a fermented *Aspergillus oryzae* JAAS-32 sample.

To achieve the above object, the present invention adopts the following technical solution:

A first aspect of the present invention is to provide an *Aspergillus oryzae* JAAS-32 which was deposited in Guangdong Microbial Culture Collection Center on Aug. 10, 2023 with the accession number of GDMCC No: 63725, classified and named *Aspergillus oryzae*.

A second aspect of the present invention is to provide a method for preparing a larval Hermetia illucens paste protein peptide using *Aspergillus oryzae* JAAS-32, including the following steps: (1) preparing a larval Hermetia illucens paste, and fermenting *Aspergillus oryzae* JAAS-32 to obtain a fermented *Aspergillus oryzae* sample; and (2) mixing the larval Hermetia illucens paste with the fermented *Aspergillus oryzae* sample well, and performing enzymatic fermentation to obtain an enzymatic fermentation liquor of the larval Hermetia illucens paste.

Preferably, in the step (1), larval Hermetia illucens and water are mixed in a mass ratio of 5:4-15:4 and homogenized to prepare the larval Hermetia illucens paste.

More preferably, Hermetia illucens larvae and water are mixed in a mass ratio of 5:2 and homogenized, i.e., 200.0 g of larval Hermetia illucens are weighed, added with 80.0 mL of deionized water, and then homogenized in a homogenizer.

More preferably, the Hermetia illucens are Hermetia illucens larvae, and further preferably, Hermetia illucens larvae aged in five days.

Preferably, in the step (1), an *Aspergillus oryzae* JAAS-32 single colony is picked and inoculated into a PDA liquid medium for culture at a temperature of 30-40° C. and a stirring speed of 100-200 rpm for 48-96 hours, to obtain an *Aspergillus oryzae* seed solution; the *Aspergillus oryzae* seed solution is inoculated into a fermentation tank containing a PDA liquid medium in an inoculum size of a volume ratio of 5%-20% for culture at a temperature of 30-40° C., a stirring speed of 100-400 rpm, and an air aeration volume of 0.2-2 vvm for 48-96 hours, to obtain the fermented *Aspergillus oryzae* sample. At this time, *Aspergillus oryzae* in the fermented *Aspergillus oryzae* sample has a concentration of $1\times10^7 - 1\times10^8$ CFU/mL.

Preferably, in the step (2), 3-10 mL of the fermented *Aspergillus oryzae* sample is added per 100 g of the larval Hermetia illucens paste; and/or the enzymatic fermentation is performed at a temperature of 25-35° C. for 20-40 hours.

More preferably, 5 mL of the fermented *Aspergillus oryzae* sample is added per 100 g of the larval Hermetia illucens paste.

A third aspect of the present invention is to provide a larval Hermetia illucens paste protein peptide prepared by the aforesaid method.

Preferably, the larval Hermetia illucens paste protein peptide has a molecular weight of less than 10 kDa.

More preferably, the molecular weight of the larval Hermetia illucens paste protein peptide ranges from 1 kDa to 10 kDa, and further preferably, ranges from 3 kDa to 10 kDa.

A fourth aspect of the present invention is to provide use of the aforesaid larval Hermetia illucens paste protein peptide in preparation of an antioxidative and/or antibacterial product.

Preferably, the antibacterial includes inhibition to *Staphylococcus aureus, Escherichia coli*, and *Vibrio alginolyticus*.

Preferably, the antioxidative and/or antibacterial product includes but is not limited to feed additives.

A fifth aspect of the present invention is to provide use of the aforesaid *Aspergillus oryzae* JAAS-32 in improving a content and antibacterial performance of a larval Hermetia illucens paste protein peptide.

Advantageous effects of the present invention are as follows: The present invention screens to obtain an *Aspergillus oryzae JAAS-32 with an accession number of GDMCC No: 63725. A larval Hermetia illucens paste is subjected to enzymatic fermentation by the *Aspergillus oryzae* JAAS-32 provided by the present invention for 20-40 hours; the content of the protein polypeptide (<10 kDa) is 1.53 times that of the untreated group; the content of the free amino acids is 1.41 times that of the untreated group; the total antioxidant activity is 1.35 times that of the untreated group; and diameters of inhibition zones against *Staphylococcus aureus*, *Escherichia coli*, and *Vibrio alginolyticus* are 1.62, 1.17, and 1.45 times those of the untreated group, respectively. The strain is cultured readily, fast in growth, and well-adapted. A low-cost, easy-to-operate, and efficient process for enhancing antibacterial properties of the larval Hermetia illucens paste can be established on the basis of the strain.

DESCRIPTION OF THE EMBODIMENTS

Figure 1:
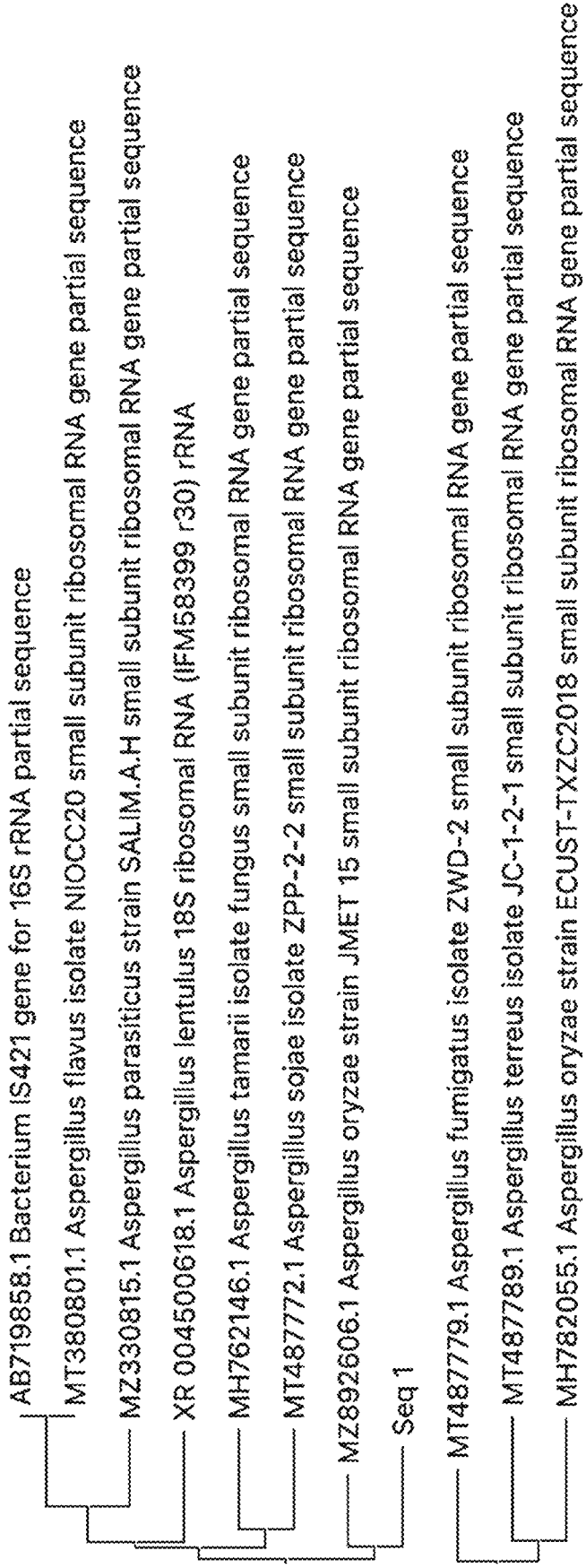
FIG. 1 shows a phylogenetic tree constructed on the basis of an ITS sequence.

To specify the present invention more clearly, the present invention will be further described specifically in combination with the examples and with reference to the accompanying drawings. It should be understood by those skilled in the art that the content described specifically below is illustrative, but not restrictive and thus, should be not construed as limiting the protection scope of the present invention.

The strain *Aspergillus oryzae* JAAS-32 provided by the present invention was deposited in Guangdong Microbial Culture Collection Center (GDMCC for short, address: 5th Floor, No. 59 Building, No. 100 Courtyard, Xianlie Mid. Rd., Institute of Microbiology, Guangdong Academy of Sciences, postcode: 510070) on Aug. 10, 2023 with the accession number of GDMCC No. 63725, classified and named *Aspergillus oryzae*. *Aspergillus oryzae* JAAS-32 GDMCC No. 63725 is abbreviated *Aspergillus oryzae* JAAS-32.

In the following examples, the PDA liquid medium contains the following components of 6.0 g/L powdered potato extract, 20.0 g/L glucose, and 0.1 g/L chloramphenicol, with a pH value of 5.4-5.8.

The PDA solid plate is namely obtained by adding 15 g/L agar to a PDA liquid medium.

Article number (Art. No.) of *Staphylococcus aureus*: CICC 10306; Art. No. of *Escherichia coli*: CICC 10372; Art. No. of *Vibrio alginolyticus*: CICC 10484.

Example 1 Screening, Identification, and Enzyme Activity Assay of *Aspergillus oryzae*

1. Isolation and Purification of Culture (1) 200.0 g fresh Hermetia illucens larvae fed with kitchen wastes were weighed and homogenized. 200.0 g of the homogenized Hermetia illucens larvae were weighed, added with 80.0 mL deionized water, and oscillated for 1 hour at 30.0° C. and 200 rpm, then taken out and subjected to standing for 30 minutes.

(2) Supernatant was taken and diluted with sterile water in gradients to 105 CFU/mL, and then the diluted bacterial suspension was coated on a PDA solid plate. The PDA solid plate was invertedly cultured for 24 hours at a constant temperature of 30° C.; single colonies were picked from the plate and repeatedly coated on the PDA solid plate, to obtain a pure culture.

2. Identification of the Strain

The screened fungi were subjected to ITS sequencing. A column-type DNA method (a column-type DNA extraction kit was purchased from Sangon Biotech (Shanghai) Co., Ltd.) was used to extract genomic DNA of fungi; the extracted DNA was PCR amplified using ITS amplification primers ITS1 and ITS4.

The ITS1 sequence is: 5'-TCCGTAGGT-GAACCTGCGG-3' (SEQ ID No.1), and the ITS4 sequence is: 5'-TCCTCCGCTTATTGATATGC-3' (SEQ ID No.2). The PCR amplification system is shown in Table 1; and PCR procedure is shown in Table 2.

TABLE 1

PCR amplification system

| Reagent | Dose (μL) |
| --- | --- |
| Primer ITS1 | 1.5 |
| Primer ITS4 | 1.5 |
| ddH$_2$O | 20.5 |
| Mastermix | 15 |
| DNA template | 1.5 |

TABLE 2

PCR amplification procedure

| Step | Condition |
| --- | --- |
| Predenaturation | 95° C., 5 min |
| Denaturation | 95° C., 30 s |
| Annealing | 57° C., 30 s |
| Extension | 72° C., 1 min 30 s |
| Final extension | 72° C., 7 min |
| Preservation | 4° C. |

Note: there are three procedures of cyclic denaturation-annealing-extension, 30 cycles in total.

The PCR amplified product was sent to General Biol (Anhui) Co., Ltd for sequencing, and the gene sequence of the sequenced ITS fragment is shown in SEQ ID No. 3 and subjected to homology alignment with NCBI database; MGEA 11 was used to construct a phylogenetic tree; see details in FIG. 1. As can be seen from FIG. 1, the strain was identified as *Aspergillus oryzae*.

The gene sequence of the ITS fragment is shown in the following SEQ ID No. 3:

GATTTCTCGTAAGGTGCCGAGCGGGTCATCATAGAAACACCGCCCGATC

CCTAGTCGGCATAGTTTATGGTTAAGACTACGACGGTATCTGATCGTCT

TCGATCCCCTAACTTTCGTTCCCTGATTAATGAAAACATCCTTGGCGAA

TGCTTTCGCAGTAGTTAGTCTTCAGCAAATCCAAGAATTTCACCTCTGA

-continued
CAGCTGAATACTGACGCCCCGACTATCCCTATTAATCATTACGGCGGT

CCTAGAAACCAACAAAATAGAACCGCACGTCCTATTCTATTATTCCATG

CTAATGTATTCGAGCAAAGGCCTGCTTTGAACACTCTAATTTTTTCACA

GTAAAAGTCCTGGTTCCCCCCACAGCCAGTGAAGGCCATGAGGTTCCCC

AGAAGGAAAGGTCCAGCCGGACCAGTACTCGCGGTGAGGCGGACCGGCC

AGCCAGACCCAAGGTTCAACTACGAGCTTTTTAACTGCAACAACTTTAA

TATACGCTATTGGAGCTGGAATTACCGCGGCTGCTGGCACCAGACTTGC

CCTCCAATTGTTCCTCGTTAAGGGATTTAGATTGTACTCATTCCAATTA

CGAGACCCAAAAGAGCCCCGTATCAGTATTTATTGTCACTACCTCCCCG

TGTCGGGATTGGGTAATTTGCGCGCCTGCTGCCTTCCTTGGATGTGGGT

AGCCCGTTTCTCAGGCTCCCTCTCCGGAATCGAACCCTAATTCCCCGTT

ACCCGTTGCCACCATGGTAGGCCACTATCCTACCATCGAAAGTTGATAG

GGCAGAAATTTGAATGAACCATCGCCGGCGCAAGGCCATGCGATTCGTT

AAGTTATTATGAATCACCAAGGAGCCCCGAAGGGCATTGGTTTTTTATC

TAATAAATACACCCCTTCCGAAGTCGAGGTTTTTAGCATGTATTAGCTC

TAGAATTACCACAGGTATCCATGTAGTAAGGTACTATCAAATAAACGAT

AACTGATTTAATGAGCCATTCGC

3. Determination of *Aspergillus oryzae* Protein Hydrolysis Circle (1) Preparation of an *Aspergillus oryzae* JAAS-32 Solution A frozen *Aspergillus oryzae* JAAS-32 strain was taken out of a −80° C. refrigerator. The strain was coated on a PDA solid plate and cultured for 24 hours at 30° C. 1-2 circles of the *Aspergillus oryzae* single colonies were taken out of the PDA solid plate and inoculated into 100 mL of a PDA liquid medium, and then cultured in a thermostatic incubator (30° C., 200 rpm) for 24 hours, to obtain the *Aspergillus oryzae* JAAS-32 solution.

(2) *Aspergillus oryzae* Protein Hydrolysis Circle

Figure 2:
FIG. 2 shows a protein hydrolysis circle of an *Aspergillus oryzae* JAAS-32.
Figure 3:
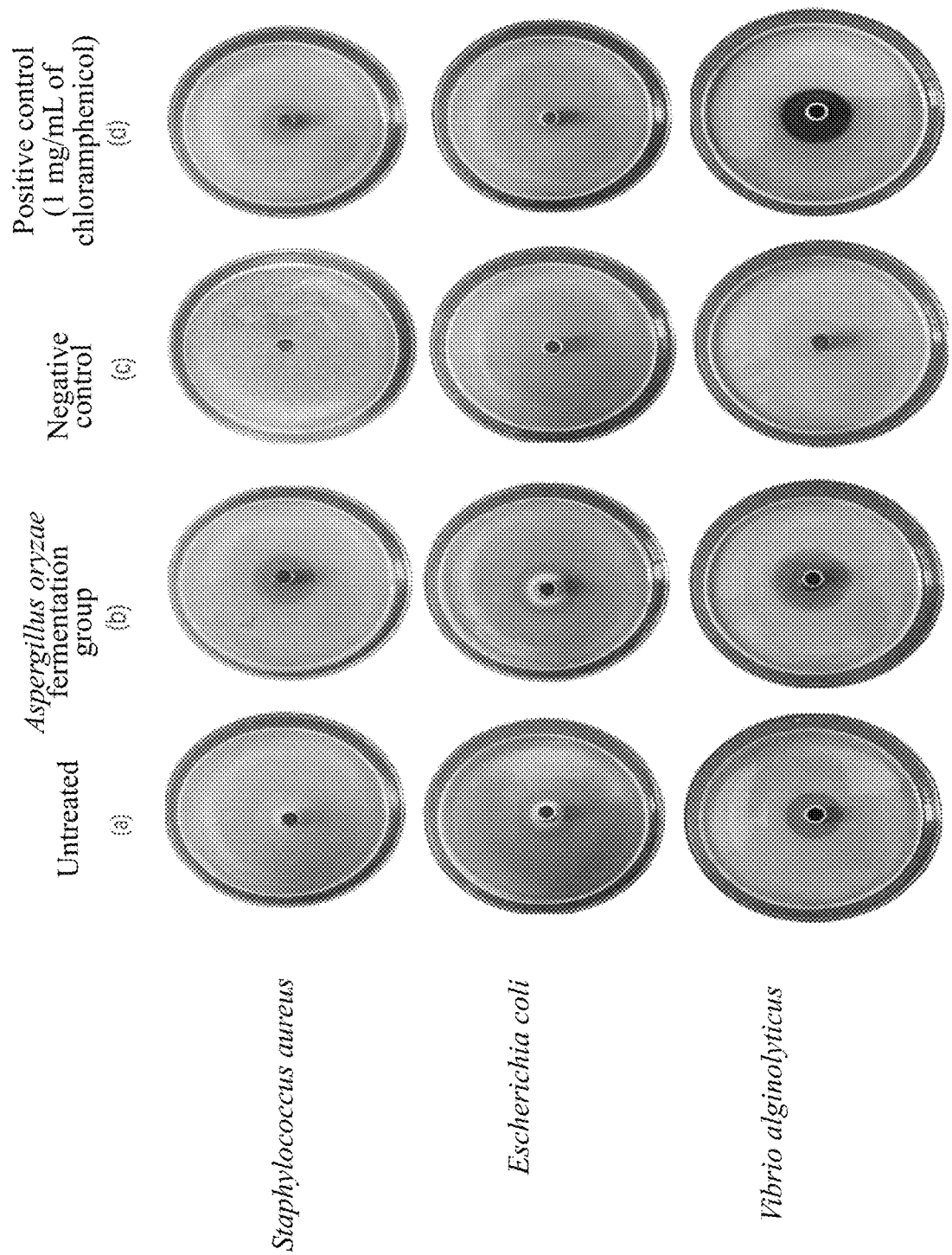
FIG. 3 shows diameter determination of inhibition zones of an antibacterial Hermetia illucens peptides to pathogenic bacteria: a, antibacterial Hermetia illucens peptide in an untreated group; b, antibacterial Hermetia illucens peptide in an *Aspergillus oryzae* fermentation group; c, sterile water in negative control; and d, chloramphenicol aqueous solution in positive control.

A proper amount of the *Aspergillus oryzae* JAAS-32 solution was absorbed, and slightly dotted on a protease screening plate (the protease screening plate contains the components of 20 g/L skimmed milk, and 20 g/L agar), invertedly cultured for 24 hours at 30° C. to observe and determine the diameter of the *Aspergillus oryzae* protein hydrolysis circle. As shown in FIG. 2, the result shows that the diameter of the *Aspergillus oryzae* protein hydrolysis circle is 25±0.2 mm.

4. Enzymatic Activity Assay of Total *Aspergillus oryzae* Proteases

The *Aspergillus oryzae* JAAS-32 solution was subjected to enzymatic activity assay of proteases with a kit for enzymatic activity assay of total proteases from Nanjing Jiancheng Bioengineering Institute, and the enzymatic activity was 1.104 azocasein/h/mg.

Example 2 *Aspergillus oryzae* Enzymolysis Process of the Larval Hermetia Illucens Paste 1. Preparation of the Larval Hermetia Illucens Paste 200.0 g of fresh Hermetia illucens larvae which were fed with kitchen wastes and aged in five days were weighed, added with 80.0 mL of sterile water and homogenized in a homogenizer, to obtain the larval Hermetia illucens paste.

2. Fermentation of *Aspergillus oryzae* JAAS-32 to obtain a fermented *Aspergillus oryzae* sample

*Aspergillus oryzae* JAAS-32 was streak inoculated onto a PDA solid plate and cultured for 24 hours at 30° C. to obtain activated *Aspergillus oryzae* JAAS-32 single colonies. The *Aspergillus oryzae* JAAS-32 single colonies were picked and inoculated into a PDA liquid medium for culture at a temperature of 30° C. and a stirring speed of 150 rpm for 60 hours, to obtain an *Aspergillus oryzae* seed solution; the seed solution was inoculated into a fermentation tank containing a PDA liquid medium in an inoculum size of 10% of a volume ratio for culture at a temperature of 30° C., a stirring speed of 300 rpm, and an air aeration volume of 0.4 vvm for 60 hours, to obtain the fermented *Aspergillus oryzae* JAAS-32 sample.

3. Fermentation of the Larval Hermetia Illucens Paste by *Aspergillus oryzae*

100.0 g of the larval Hermetia illucens paste was weighed, added with 5 mL of the fermented *Aspergillus oryzae* sample and mixed well, then put in a thermostatic incubator (30.0° C., 200 rpm) and fermented for 24 hours, to obtain a fermentation liquor of larval Hermetia illucens paste in the *Aspergillus oryzae* fermentation group.

Moreover, 100.0 g of the larval Hermetia illucens paste was weighed, put to a thermostatic incubator (30.0° C., 200 rpm) and fermented for 24 hours, to obtain a fermentation liquor of larval Hermetia illucens paste in the untreated group.

4. Dialysis of the Hermetia Illucens Protein Polypeptide (<10 kDa) by a Dialysis Bag (1) Pretreatment of a Dialysis Bag:

A dialysis bag having a molecular weight cut-off of 10 kDa was cut into small segments having a length of 11 cm, and boiled with EDTA (pH=8.0) before use to wash off surface impurity, and then taken out, washed thoroughly with distilled water, to ensure no cleaning agent or impurity residual on the surface of the dialysis bag.

(2) Dialysis and Content Determination of the Protein Polypeptide (<10 kDa):

The fermentation liquor of larval Hermetia illucens paste obtained in step 3 was taken out and put in the dialysis bag, and both ends of the dialysis bag were clamped with a dialysis clamp or ribbon. The dialysis bag containing the larval Hermetia illucens paste was put to a beaker and added with 50 mL of distilled water to ensure that the dialysis bag was completely soaked into the distilled water for dialysis for 36 hours, and distilled water was replaced once every 12 hours. At the end of the dialysis, three times of the dialysate were mixed to determine the content of the protein peptide therein by a BCA process, and to determine the content of the free amino acids by a kit for free amino acid content (purchased from Grace Biotechnology Co., Ltd, Suzhou, China).

Test result:

The *Aspergillus oryzae* fermentation group in this example has an increased content of protein polypeptide (<10 kDa) and an increased content of free amino acids, as compared to the fermentation liquor of larval Hermetia illucens paste in the untreated group. As can be seen from Table 3, the content of protein polypeptide (<10 kDa) in the *Aspergillus oryzae* fermentation group is 1.53 times that of the untreated group, and the content of free amino acids is 1.41 times that of the untreated group. It indicates that macromolecular proteins may be subjected to enzymolysis with the protease secreted by *Aspergillus oryzae* into polypeptides and amino acids.

TABLE 3

Content of the protein peptides and free amino acids in the larval *Hermetia illucens* pastes of the untreated group and the *Aspergillus oryzae* fermentation group

| Name | Protein polypeptide <10 kDa (mg/g) | Free amino acid (mg/g) |
|---|---|---|
| Untreated group | 118.400 | 30.571 |
| *Aspergillus oryzae* fermentation group | 181.020 | 43.215 |

Test Example 1 Detection for the total antioxidant activity of the larval Hermetia illucens paste protein peptide The lyophilized powder of the larval Hermetia illucens paste protein polypeptide (<10 kDa) prepared in the *Aspergillus oryzae* fermentation group of Example 2 was taken out and prepared to series of solutions having a concentration of 10 mg/mL by ultrapure water; the total antioxidant capacity assay was performed according to the method of the instructions of the total antioxidant capacity assay kit (purchased from Nanjing Jiancheng Bioengineering Institute).

Test result: the larval Hermetia illucens paste protein peptides prepared both in the untreated group and the *Aspergillus oryzae* fermentation group all show antioxidant activity; when the concentration of the Hermetia illucens protein polypeptide (<10 kDa) is 10 mg/g, as shown in Table 4, the total antioxidant capacity in the untreated group is 26.81 U/mg, and the total antioxidant capacity in the *Aspergillus oryzae* fermentation group is 36.18 U/mg, which is 1.35 times that of the untreated group.

TABLE 4

Total antioxidant activity of the larval *Hermetia illucens* paste protein peptide

| Treatment condition | Total antioxidant activity U/mg |
|---|---|
| Untreated group | 26.81 |
| *Aspergillus oryzae* enzymatic fermentation group | 36.18 |

Test Example 2 Detection for the antibacterial activity of the larval Hermetia illucens paste protein peptide 1. Extraction of the Antibacterial Peptide of the Larval Hermetia Illucens Paste (1) Preparation of an antibacterial peptide extraction solution (10% acetic acid and 0.01 mol/L $Na_2EDTA$).

(2) The fermentation liquor of larval Hermetia illucens paste in the untreated group and the *Aspergillus oryzae* fermentation group of Example 2 was mixed with the antibacterial peptide extraction solution well (v: v=1:10), respectively, and liquid-solid extracted for half an hour at 200 rpm and 37° C., then transferred to a centrifugal machine (3500 rpm, 25 min); supernatant was collected as a crude extraction solution of the antibacterial peptide. The crude extraction solution was further frozen-dried to obtain the antibacterial Hermetia illucens peptide.

2. Determination of Antibacterial Activity of the Antibacterial Hermetia Illucens Peptide The negative control was sterile water, the antibiotic chloramphenicol served as a positive control and was prepared to a chloramphenicol aqueous solution having a concentration of 0.5 mg/mL. The concentration of the *Staphylococcus aureus* solution and *Escherichia coli* solution as well as *Vibrio alginolyticus* solution was determined $1.0 \times 10^9$ CFU/mL, $1.0 \times 10^9$ CFU/mL, and $1.0 \times 10^7$ CFU/mL, respectively; proper amount of the *Staphylococcus aureus* solution and *Escherichia coli* solution were absorbed and evenly coated on LB media, and the *Vibrio alginolyticus* solution was coated on a TCBS plate. An Oxford cup having a diameter of 7.5 mm was slightly placed on the LB plate, added with an equivalent amount of the antibacterial Hermetia illucens peptide, and cultured in a 37° C. thermostatic incubator for 10 hours, then the diameter of inhibition zones was observed and measured.

Test result: the antibacterial Hermetia illucens peptide was subjected to in vitro antibacterial test. The antibacterial effect is as follows: as can be seen from Table 5, inhibition zones appear both in the untreated group and the *Aspergillus oryzae* fermentation group; the inhibition zones against *Staphylococcus aureus*, *Escherichia coli*, and *Vibrio alginolyticus* are 16±0.1 mm, 24±0.1 mm, and 20±0.2 mm in the untreated group, respectively; the inhibition zones against *Staphylococcus aureus*, *Escherichia coli*, and *Vibrio alginolyticus* are 26±0.2 mm, 28±0.1 mm, and 29±0.2 mm in the *Aspergillus oryzae* fermentation group, respectively; the diameter of the inhibition zones is 1.62 times, 1.17 times, and 1.45 times that of the untreated group, respectively. The test result indicates that the larval Hermetia illucens paste has significantly improved antibacterial performance after enzymatic fermentation by *Aspergillus oryzae*.

TABLE 5

Antibacterial activity of the antibacterial *Hermetia illucens* peptide

| | Diameter of inhibition zone (mm) | | | |
|---|---|---|---|---|
| Bacterium | Untreated group (a) | *Aspergillus oryzae* fermentation group (b) | Negative control (c) | Positive control (1 mg/ml of chloramphenicol) (d) |
| *Staphylococcus aureus* | 16 | 26 | | 16 |
| *Escherichia coli* | 24 | 28 | 0 | 17 |
| *Vibrio alginolyticus* | 20 | 29 | | 26 |

Obviously, the aforesaid examples of the present invention are merely illustrative of the examples given in the present invention more clearly but are not construed as limiting the embodiments of the present invention. Based on the aforesaid description, those skilled in the art could further make other different forms of changes or alterations. All the implementation methods may be not exhaustively enumerated here. Any obvious change or alteration elicited from the technical solutions of the present invention shall still fall within the protection scope of the present invention.

What is claimed is:

1. A method for preparing a larval Hermetia illucens paste protein peptide using an *Aspergillus oryzae* JAAS-32, which was deposited in Guangdong Microbial Culture Collection Center on Aug. 10, 2023 with an accession number of GDMCC No: 63725, the method comprising the following steps: (1) preparing a larval Hermetia illucens paste, and fermenting *Aspergillus oryzae* JAAS-32 to obtain a fermented *Aspergillus oryzae* sample; and (2) mixing the larval Hermetia illucens paste with the fermented *Aspergillus oryzae* sample, and fermenting the mixture to obtain a fermentation liquor of the larval Hermetia illucens paste.

2. The method according to claim 1, wherein in the step (1), Hermetia illucens larvae and water are mixed in a mass ratio of 5:4-15:4 and homogenized to prepare the larval Hermetia illucens paste.

3. The method according to claim 1, wherein in the step (1), an *Aspergillus oryzae* JAAS-32 single colony is picked and inoculated into a potato dextrose agar (PDA) liquid medium and cultured at a temperature of 30-40° C. and a stirring speed of 100-200 rpm for 48-96 hours, to obtain an *Aspergillus oryzae* seed solution; the *Aspergillus oryzae* seed solution is inoculated into a fermentation tank containing a PDA liquid medium in an inoculum size to volume ratio of 5%-20% and cultured at a temperature of 30-40° C., a stirring speed of 100-400 rpm, and an air aeration volume of 0.2-2 vvm for 48-96 hours, to obtain the fermented *Aspergillus oryzae* sample.

4. The preparation method according to claim 1, wherein in the step (2), 3-10 mL of the fermented *Aspergillus oryzae* sample is added per 100 g of the larval Hermetia illucens paste; and/or the fermentation is performed at a temperature of 25-35° C. for 20-40 hours.

* * * * *